(12) United States Patent
Goyal et al.

(10) Patent No.: US 12,378,171 B2
(45) Date of Patent: Aug. 5, 2025

(54) PROCESSES AND APPARATUSES FOR SEPARATING CHLORIDES FROM N-BUTANE

(71) Applicant: UOP LLC, Des Plaines, IL (US)

(72) Inventors: Amit Goyal, Haryana (IN); Gregory J. Schrad, Winfield, IL (US); Gregory R. Werba, Arlington Heights, IL (US); Sean Mann, Chicago, IL (US); Christine Marie Long, El Cerrito, CA (US); Cynthia M. Kwik, Sugar Land, TX (US)

(73) Assignee: UOP LLC, Des Plaines, IL (US)

( * ) Notice: Subject to any disclaimer, the term of this patent is extended or adjusted under 35 U.S.C. 154(b) by 82 days.

(21) Appl. No.: 18/512,747

(22) Filed: Nov. 17, 2023

(65) Prior Publication Data

US 2024/0166583 A1 May 23, 2024

Related U.S. Application Data

(60) Provisional application No. 63/384,283, filed on Nov. 18, 2022.

(51) Int. Cl.
*C07C 7/09* (2006.01)
*B01D 3/14* (2006.01)
(Continued)

(52) U.S. Cl.
CPC ............... *C07C 7/09* (2013.01); *B01D 3/143* (2013.01); *B01D 53/02* (2013.01); *C07C 7/12* (2013.01);
(Continued)

(58) Field of Classification Search
None
See application file for complete search history.

(56) References Cited

U.S. PATENT DOCUMENTS 2,366,117 A * 12/1944 Leonard ............... C07C 5/2789
585/737
2,371,477 A * 3/1945 Souders, Jr. ............ B01J 12/00
422/615
(Continued)

FOREIGN PATENT DOCUMENTS

CN 101244972 A 8/2008
CN 106929093 A 7/2017
(Continued)

OTHER PUBLICATIONS

Nguyen Van Duc Long et al., Design and optimization of heat integrated dividing wall columns for improved debutanizing and deisobutanizing fractionation of NGL, Korean J. Chem. Eng., 30(2), 286-294 (2013).
(Continued)

*Primary Examiner* — Tam M Nguyen (57) ABSTRACT

Processes and apparatuses for separating chlorides from a butane product stream by removing chlorides from a portion of said feed stream in a rectification section of the separation zone. The rectification section may be in a rectification column which may be combined with a stripper column. Alternatively, a wall may be used to provide the rectification section in a fractionation column. The processes and apparatuses can be used in both new designs and revamped designs.

20 Claims, 10 Drawing Sheets (51) Int. Cl.
  *B01D 53/02* (2006.01)
  *C07C 7/04* (2006.01)
  *C07C 7/12* (2006.01)

(52) U.S. Cl.
  CPC .. *B01D 2256/24* (2013.01); *B01D 2257/2025* (2013.01)

(56) References Cited

U.S. PATENT DOCUMENTS

| | | | |
|---|---|---|---|
| 2,418,146 A * | 4/1947 | Upham | C07C 9/16 585/905 |
| 3,873,635 A | 3/1975 | Prescott et al. | |
| 4,218,575 A | 8/1980 | Webb, Jr. | |
| 7,439,410 B1 | 10/2008 | Rice et al. | |
| 8,198,499 B2 | 6/2012 | Luo et al. | |
| 8,728,301 B2 | 5/2014 | Timken | |
| 9,446,996 B2 | 9/2016 | Fang et al. | |
| 9,802,186 B2 | 10/2017 | Luo et al. | |
| 10,005,057 B1 | 6/2018 | Girgis et al. | |
| 2001/0034468 A1 * | 10/2001 | Mauleon | C07C 9/00 585/719 |
| 2004/0260132 A1 * | 12/2004 | Walsdorff | C07C 5/367 585/317 |
| 2008/0242904 A1 * | 10/2008 | Rice | C07C 9/16 585/311 |
| 2013/0062253 A1 | 3/2013 | Timken | |
| 2019/0352240 A1 | 11/2019 | Jo et al. | |
| 2021/0048244 A1 * | 2/2021 | Temple | B01D 5/009 |

FOREIGN PATENT DOCUMENTS

| | | |
|---|---|---|
| CN | 207627960 U | 7/2018 |
| CN | 109107521 A | 1/2019 |
| CN | 113828001 A | 12/2021 |
| GB | 801145 | 9/1958 |
| GB | 1567835 | 5/1980 |
| WO | 2014022056 A1 | 2/2014 |
| WO | 2018135712 A2 | 7/2018 |

OTHER PUBLICATIONS

International Search Report from corresponding PCT application PCT/US2023/079512, mailed Mar. 15, 2024.
Written Opinion from corresponding PCT application PCT/US2023/079512, mailed Mar. 15, 2024.

* cited by examiner

PROCESSES AND APPARATUSES FOR SEPARATING CHLORIDES FROM N-BUTANE

RELATED APPLICATIONS

This application claims priority to U.S. Provisional Patent Application Ser. No 63/384,283 filed Nov. 18, 2022, the entirety of which is incorporated herein by reference.

FIELD OF THE INVENTION

This invention relates generally to processes and apparatuses for separating chlorides from n-butane, and more particularly to processes and apparatuses which use a rectification section.

BACKGROUND OF THE INVENTION

Alkylation is the reaction between feed hydrocarbons and an alkylating agent. Hydrocarbon alkylation is widely used in the petroleum refining and petrochemical industries to produce a variety of useful acyclic and cyclic hydrocarbon products used as motor fuel, plastic and detergent precursors and petrochemical feedstocks. For example, large amounts of high octane gasoline are produced commercially by alkylation of isobutane with butenes or propylene. This significantly increases the value of the C4 feed hydrocarbons.

Historically, such alkylation processes have commonly employed hydrofluoric acid (HF) or Sulfuric Acid ($H_2SO_4$) as a catalyst. Environmental and safety concerns, among other factors, have led to the development of newer processes utilizing other catalysts. For example, acidic ionic liquids have been utilized as catalysts in hydrocarbon conversion processes, such as alkylation, isomerization, disproportionation, reverse disproportionation, and oligomerization. The ionic liquid catalysts are more environmentally friendly and therefore, more desirable than the sulfuric acid and hydrofluoric acid.

While presumably effective for their intended purposes, the use of ionic liquid catalyst has surprisingly been found to lead to much higher concentrations of chlorides in the butane product stream. The high concentration of organic chlorides (butyl chloride) was not expected, and the amount of inorganic chloride (HCl) was not expected in the hot section of a fractionation column. While not intending to be bound by any theory, it is believed that the inorganic chlorides come from the decomposition of the organic chlorides.

The butane product stream is typically drawn as a sidedraw from a fractionation column, such as an isostripper, deisobutanizer, or depropanizer column and is treated in chloride treaters and dried before it can be used as regenerant or as feed or sold as final product. The hydrocarbon reactor effluent that is fed to the isostripper, deisobutanizer, or depropanizer column will contain organic (BuCl) and inorganic chlorides (HCl) which are contained in the n-butane stream recovered from same. If not controlled, these chlorides will shorten the life of chloride treater adsorbent which will need to be replaced to maintain the chloride removal efficiency.

Accordingly, it would be desirable to have more effective and efficient ways to control both the organic and inorganic chloride levels in n-butane streams.

SUMMARY OF THE INVENTION

The present invention provides multiple process schemes to control organic and inorganic chloride levels in butane product streams. Additionally, the present process schemes control the amount of C5+ in the butane product stream. For new unit designs, this invention can achieve a low total chloride content<0.5 wppm without requiring chloride treaters. For a revamp unit design, this invention allows high chloride recovery along with use of existing equipment (chloride treaters) at the site.

Therefore, the present invention may be characterized, in at least one aspect, as providing a process for separating chlorides from a butane product stream by: separating, in a separation zone, a feed stream comprising light hydrocarbons, propane, isobutane, n-butane, chlorides, and C5+ hydrocarbons into a stream comprising light hydrocarbons, propane, isobutane, and n-butane and a liquid stream comprising an alkylate effluent with C5+ hydrocarbons; and, removing chlorides from a liquid or vapor portion of said feed stream in a rectification section of the separation zone, the rectification section providing a butane product stream.

The separation zone may include a fractionation column, and the rectification section may include a rectification column. A bottoms stream from the rectification column may be passed back to the fractionation column. A side draw stream from the rectification column may be the butane product stream. An overhead stream from the rectification column may be condensed to provide the butane product stream.

The separation zone may include a fractionation column, and further includes a stripping section. The stripping section and the rectification section may be in the fractionation column. The separation zone may include a second column and both the stripping section and the rectification section may be in the second column. The separation zone may further include a first column comprising the rectification section and a second column including the stripping section. A bottoms stream from the second column may be passed to the first column. The first column and the second column may produce a common overhead stream. The first column and the second column may be disposed on top of each other. The separation zone may include a second column and the second column includes the stripping section and the fractionation column comprises the rectification section.

In some aspects, the present invention, broadly, may be characterized as providing a process for separating chlorides from a butane product stream by: separating, in a separation zone comprising a deisobutanizer column, a feed stream comprising light hydrocarbons, propane, isobutane, n-butane, chlorides, and C5+ hydrocarbons into a stream comprising light hydrocarbons, propane, isobutane, and n-butane and a liquid stream comprising an alkylate effluent with C5+ hydrocarbons; and, passing a side draw stream from the deisobutanizer column to a rectification column, the side draw stream comprising liquid or vapor; passing a bottoms stream from the rectification column to the deisobutanizer column, the bottoms stream comprising organic chlorides; passing a vapor or liquid stream from the rectification column to the deisobutanizer column or another lower pressure vessel, the vapor or liquid stream comprising HCl, iso-butane, and n-butane; recovering a butane product stream from the deisobutanizer column; and, passing the butane product stream to an adsorbent zone having an adsorbent configured to remove chlorides and provide a chloride lean butane product stream.

The butane product stream from the deisobutanizer column may be a side draw stream.

The process may also include cooling an overhead stream from the rectification column to provide the vapor or liquid stream and the butane product stream.

In some aspects, the present invention, broadly, may be characterized as providing a process for separating chlorides from an n-butane stream by: separating, in a separation zone comprising a separation column a feed stream comprising light hydrocarbons, propane, isobutane, n-butane, chlorides, and C5+ hydrocarbons into a stream comprising light hydrocarbons, propane, isobutane, and n-butane, and a liquid stream comprising an alkylate effluent with C5+ hydrocarbons; and, removing organic chlorides from the feed stream in a rectification section; and, removing HCl from the feed stream in a stripper section.

The separation zone may further include a first column having the rectification section and a second column having the stripping section.

The rectification section may be disposed within the separation column.

The separation zone includes a second column and both the stripping section and the rectification section are in the second column.

Additional aspects, embodiments, and details of the invention, all of which may be combinable in any manner, are set forth in the following detailed description of the invention.

DETAILED DESCRIPTION OF THE DRAWINGS

One or more exemplary embodiments of the present invention will be described below in conjunction with the following drawing figures, in which.

In the various Figures of the present application, the same reference numbers are used for the same features in the various aspects.

DETAILED DESCRIPTION OF THE INVENTION

As mentioned above, various processes and design configurations have been invented which control the flow of organic and inorganic chlorides in the alkylate effluent, and specifically in the butane and alkylate product streams. As noted above, the high concentration of both organic and inorganic chlorides is unexpected, particularly the high levels of inorganic chloride. In general, the present invention utilizes a rectification section or a rectification section and a stripper section to separate and control both organic and inorganic chlorides. The present inventions can be utilized in new units as well as in existing units.

The present invention maximizes HCl recovery and minimizes both organic and inorganic chlorides wppm in the butane product stream-which may allow efficient use of existing chloride treaters when revamping existing unit designs. In new design configurations, the combination of the rectification and the stripper sections provides a butane product stream with total chlorides to <0.5 wppm so that it can be sent directly to other production units without the need of chloride treaters/driers.

In one or more aspects, a stripper-rectifier column passes a vapor or liquid stream with concentrated inorganic chloride (HCl) back to the deisobutanizer and produces a butane product stream with a controlled concentration of organic/inorganic chlorides.

Additionally, in one or more aspects, a butane rich product stream is removed from the deisobutanizer column as which not only minimizes organic chloride but also decreases the deisobutanizer column reboiling duty.

With these general principles in mind, one or more embodiments of the present invention will be described with the understanding that the following description is not intended to be limiting.

Figure 1:
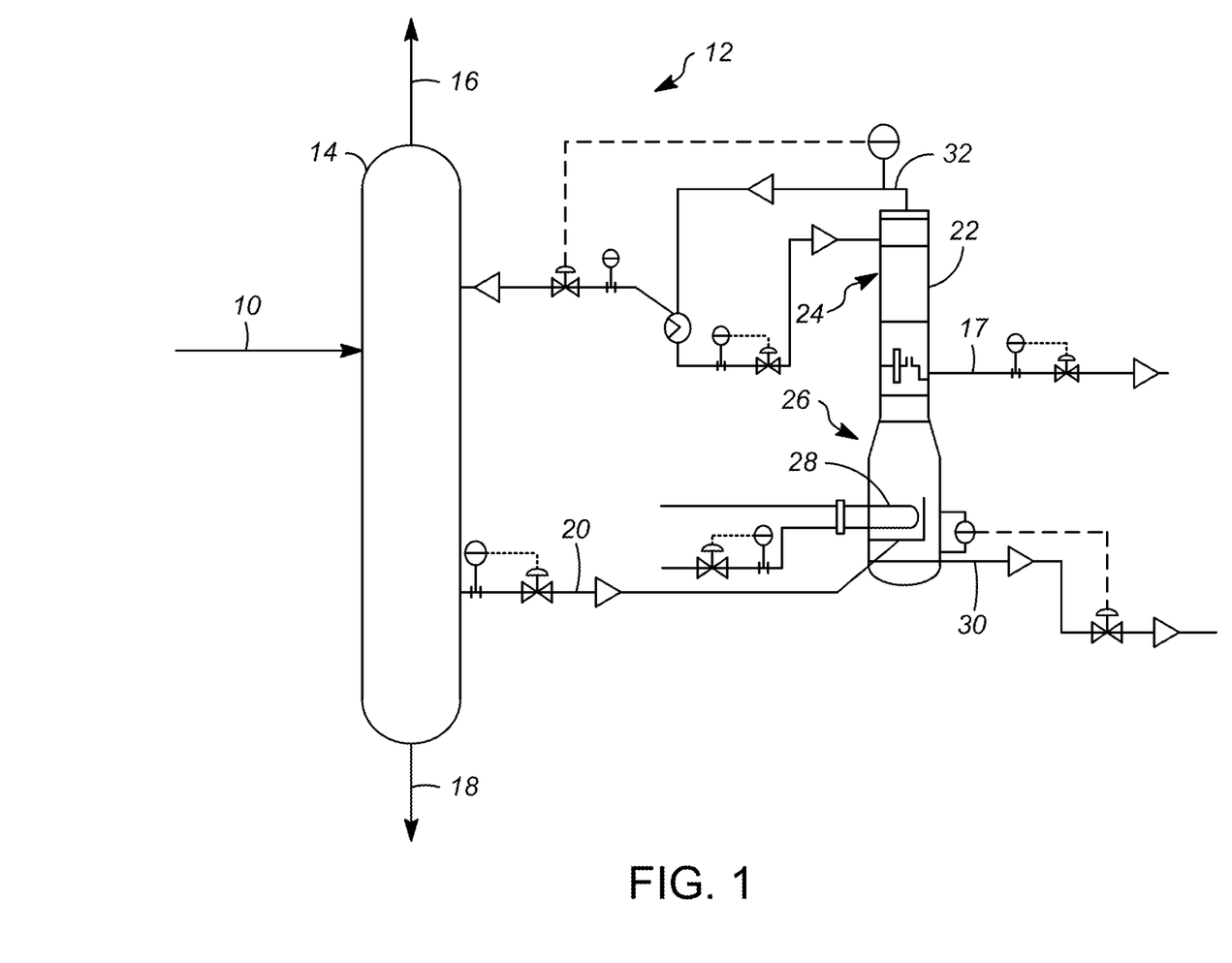
FIG. 1 is a schematic process flow diagram according to one or more aspects of the present invention.

As shown in FIG. 1, a feed stream 10 comprising light hydrocarbons, propane, isobutane, n-butane, chlorides, and C5+ hydrocarbons is passed to a separation zone 12. The feed stream 10 is preferably an effluent from an alkylation reaction zone. Such reaction zones are known in the art.

The separation zone 12 comprises a fractionation column 14 which may be a deisobutanizer column. As is known, in the fractionation column 14 the components of the feed stream 10 will separate. Accordingly, the separation zone 12 will provide a stream comprising light hydrocarbons 16 and a liquid stream 18 comprising an alkylate effluent with C5+ hydrocarbons. The stream comprising light hydrocarbons 16 may be passed to a depropanizer column and processed further as is known in the art. The alkylate effluent liquid stream 18 with C5+ hydrocarbons may also be processed further as is known in the art.

According to the various embodiments of the present invention, chlorides are removed from a liquid portion of said feed stream 10 in a rectification section of the separation zone 12 and the rectification section provides a stream 17 that is a butane product stream comprising mostly n-butane, but also isobutane, isopentane, n-pentane, and additional C6 alkylate components.

For example, with reference to FIG. 1, a liquid or vapor side draw stream 20 is withdrawn from the fractionation column 14 and passed to a rectification column 22 that is a stripper-rectifier column that has a rectification section 24 and a stripper section 26. It is contemplated that the present invention also utilizes a vapor side draw from the fractionation column 14 but a liquid stream is believed to have a lower total chloride level. The rectification column 22 receives the liquid side draw stream 20 from the fractionation column 14. A stab-in reboiler 28 or other heat source vaporizes the liquid components within the rectification column 22. Trays or a packed column facilitate the separation of the heavier components, including organic chlorides, which fall to the bottom of the rectification column 22. A bottoms stream 30 from the rectification column 22 may be returned to the fractionation column 14. Vapors pass further up in the rectification column 22 and further separate in stripper section 26. An overhead stream 32 from the rectification column 22 comprises most of the HCl and may be returned to the fractionation column 14 or to a lower pressure destination within the processing unit. The butane product stream 17 may be recovered from the stripper section 26 and passed to conventional chloride treaters.

Figure 2:
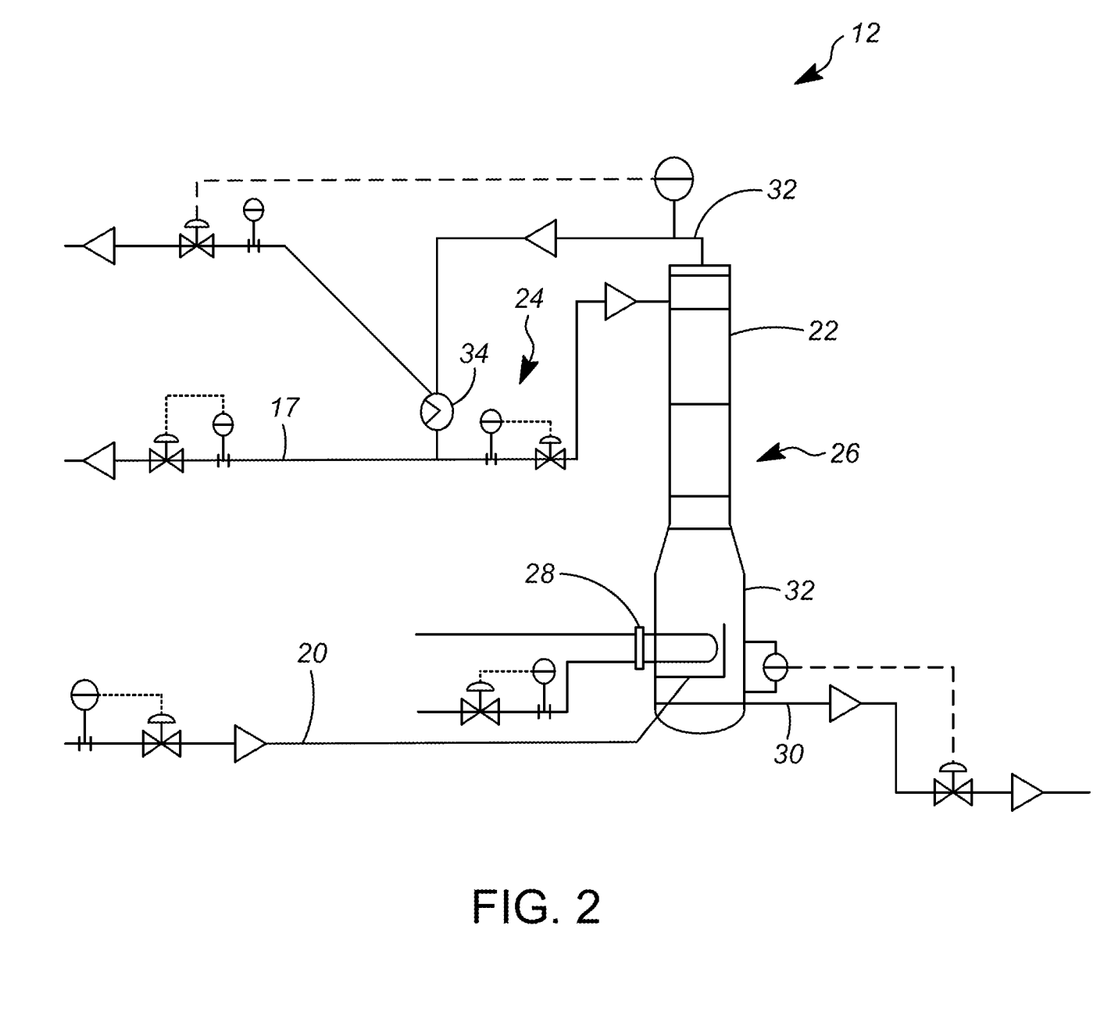
FIG. 2 is another schematic process flow diagram according to one or more aspects of the present invention.

In the embodiment of FIG. 2, the separation zone 12 again includes the rectification column 22 which receives the liquid or vapor side draw stream 20 from the fractionation column 14 (see FIG. 1). In this embodiment of FIG. 2, the overhead stream 32 from the rectification column 22 is cooled in a cooler or other exchanger 34, which facilitates separation of gaseous components and liquid components. The gaseous components 36 include HCl and may be returned to the fractionation column 14 or to another lower pressure destination within the processing unit. The liquid components from the butane product stream 17 may be recovered from the stripper section 26 and may be passed to conventional chloride treaters.

The embodiments of FIGS. 1 and 2 are preferred, but not required, to be utilized in existing alkylation units that include chloride treaters. As noted above, the present invention provides configurations that are preferably, but not necessarily, utilized in a new design.

Figure 3:
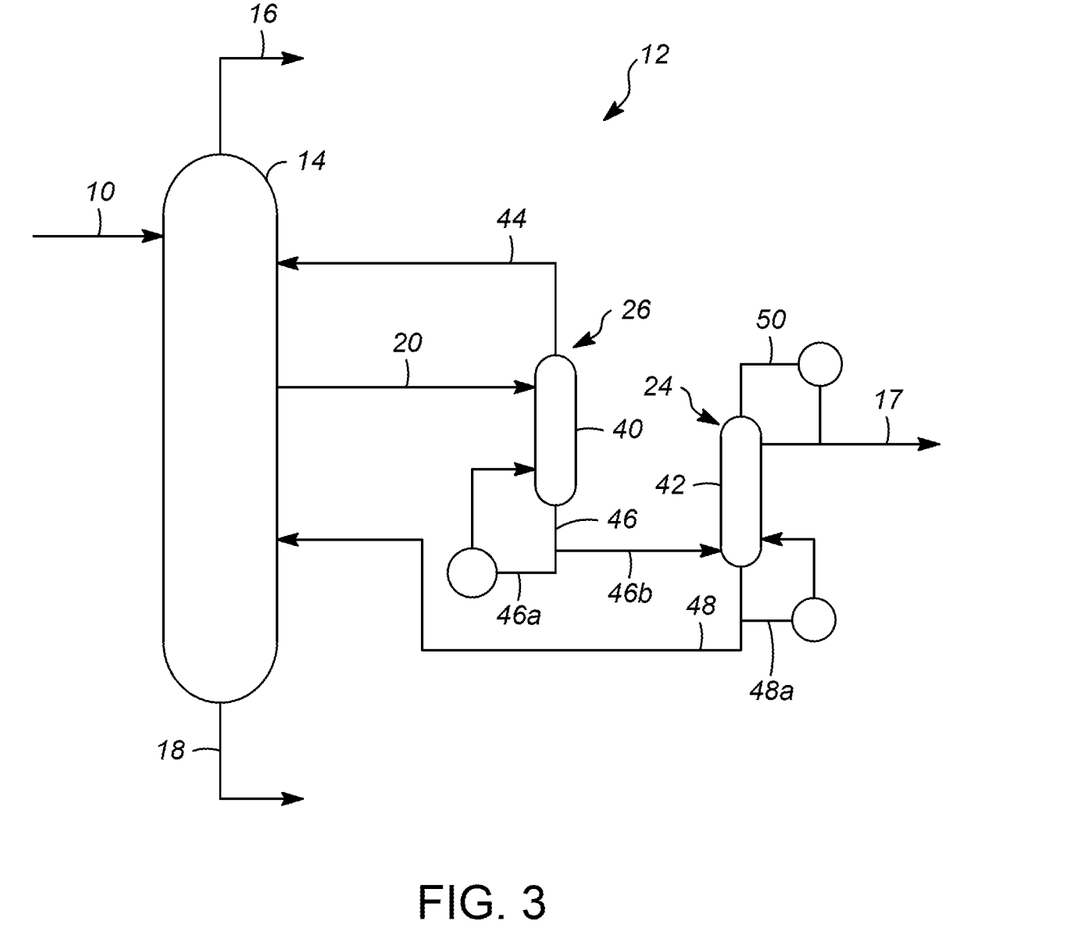
FIG. 3 is a further schematic process flow diagram according to one or more aspects of the present invention.

In FIG. 3, the separation zone 12 includes two separate columns, a stripper column 40 and a rectifier column 42. Accordingly, the liquid side draw stream 20 from the fractionation column 14 may be passed to the stripper column 40 which separates the HCl and light hydrocarbons into an HCl rich vapor stream 44 that is returned to the fractionation column 14 or to another lower pressure destination within the processing unit. A portion 46a of a bottoms stream 46 from the stripper column 40 is heated and returned to the stripper column 40. A second portion 46b of the bottoms stream 46 from the stripper column 40 is passed to the rectification column 42. In the rectification column 42, organic chlorides are separated from the n-butane. Accordingly, a bottoms stream 48 from the rectifier column 42, containing the organic chlorides and heavier hydrocarbons is returned to the fractionation column 14. A portion 48a of the bottoms stream 48 from the rectifier column 42 may be heated and returned to the rectifier column 42. An overhead stream 50 from the rectifier column 42 may be cooled in a heat exchanger 52 to provide the butane product stream 17.

Figure 4:
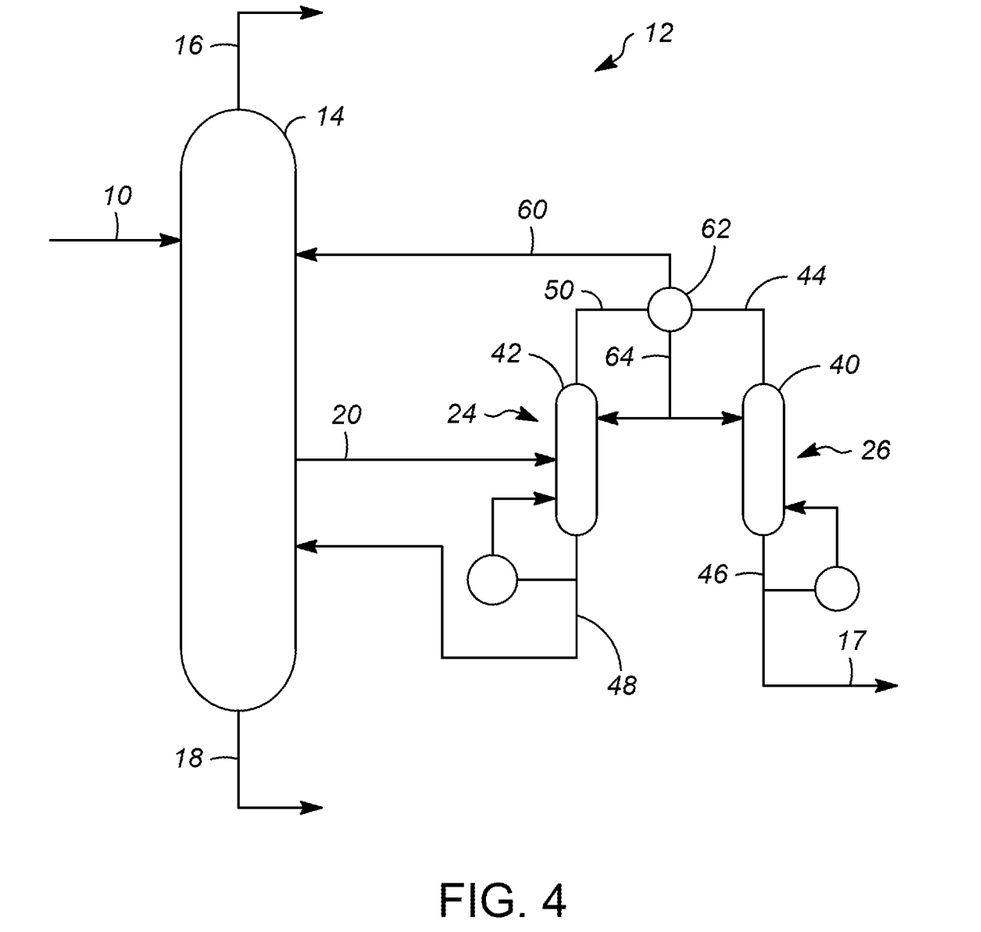
FIG. 4 is an additional schematic process flow diagram according to one or more aspects of the present invention.

Turning to FIG. 4, another embodiment is shown which includes both the stripper column 40 and the rectifier column 42. In this embodiment, the liquid side draw stream 20 is first passed to the rectifier column 42 and the two columns 40, 42 provide a common overhead stream 60. Thus, the overhead stream 50 from the rectifier column 42 and the overhead stream 44 from the stripper column 40 may be combined and passed to a condenser 62 to separate liquid components from the gaseous components. The liquid components 64 may be refluxed back to both columns 40, 42 and the gaseous components with the HCl returning to the fractionation column 14 or to another lower pressure destination within the processing unit. One particular advantage of the embodiment of FIG. 4 compared with FIG. 3, is that in FIG. 4, any HCl converted from the organic chlorides will be removed from the butane product.

Figure 5:
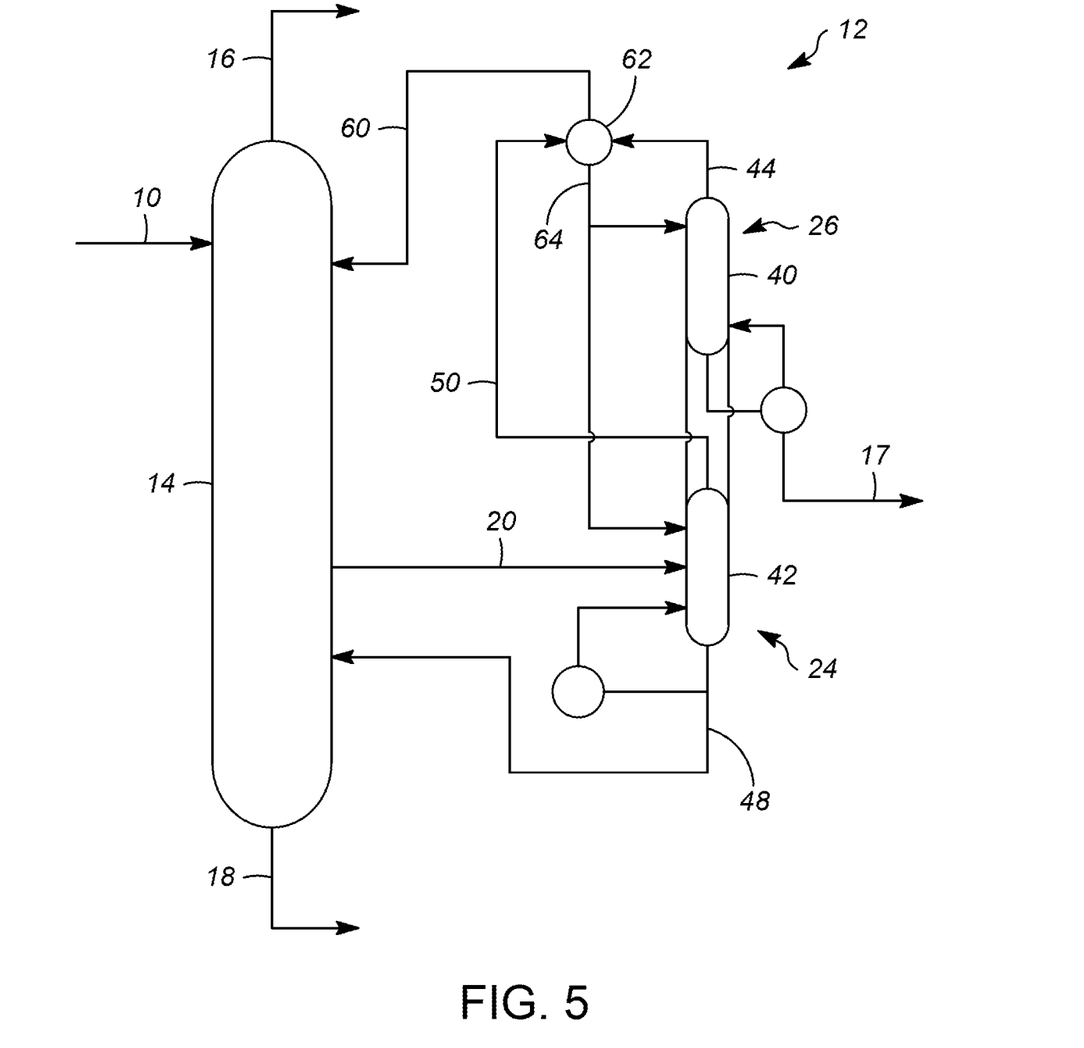
FIG. 5 is yet another schematic process flow diagram according to one or more aspects of the present invention.

In FIG. 5, another embodiment with both the stripper column 40 and the rectifier column 42, however, the two columns 40, 42 are located on top of each other. Such a configuration reduces the amount of space required for the two columns 40, 42 and, like the embodiment of FIG. 4, addresses the production of any HCl from the decomposition of organic chlorides.

Figure 6A:
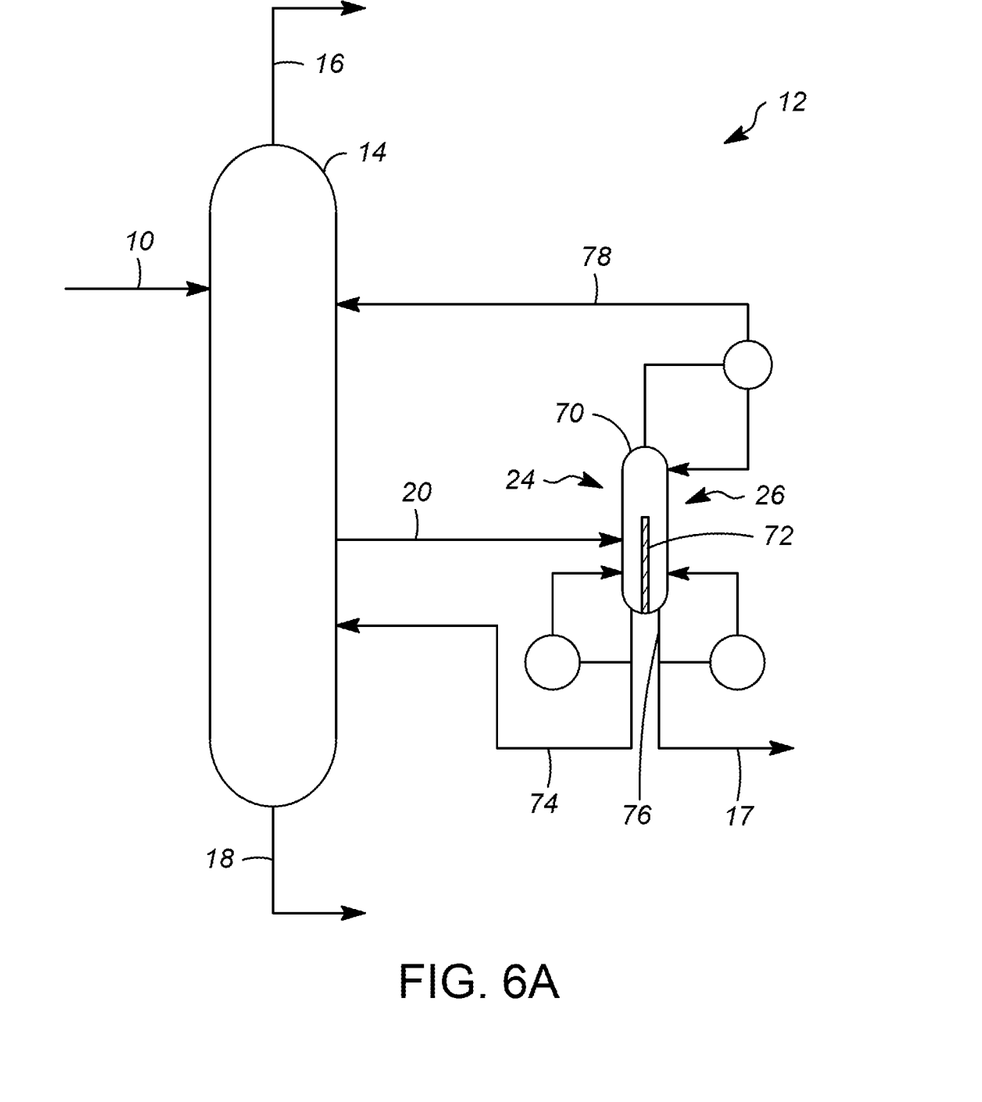
FIG. 6A is another schematic process flow diagram according to one or more aspects of the present invention.

Turning to FIG. 6A, the separation zone 12 includes the fractionation column 14 and a divided wall column 70 that includes a wall 72 splitting the bottom portion of the divided wall column 70 into two halves. Thus, the stripping section 26 and the rectification section 24 are in the same column 70. Accordingly, a bottoms stream 74 from the rectification section 24 will include the organic chloride compounds and is returned to the fractionation column 14. A bottoms stream 76 from the stripping section 26 is the butane product stream 17. A common overhead stream 78 includes HCl and is returned to the fractionation column 14 or to another lower pressure destination within the processing unit.

Figure 6B:
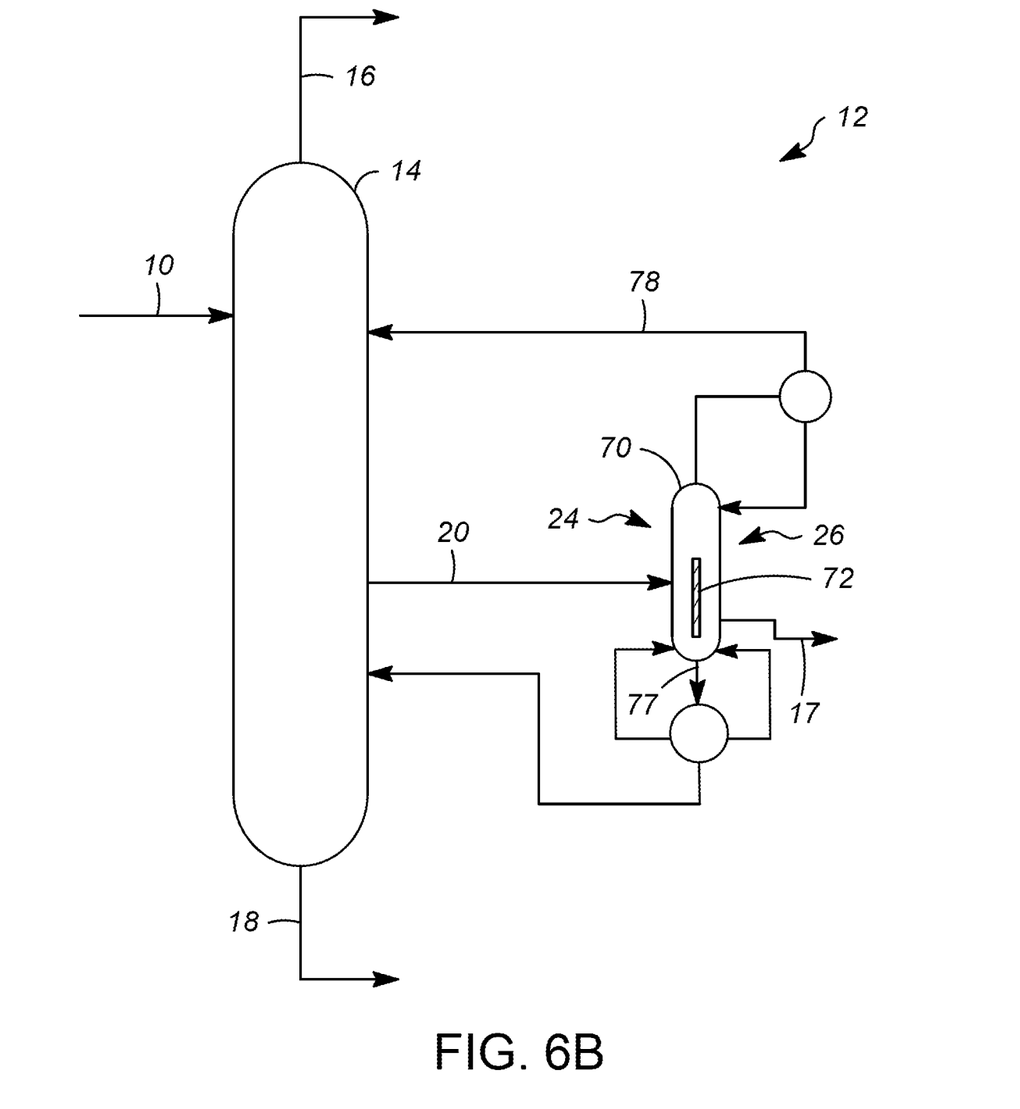
FIG. 6B is another schematic process flow diagram according to one or more aspects of the present invention.

FIG. 6B is similar to FIG. 6A, except that the wall 72 of the divided wall column 70 does not extend all the way to the bottom of the column 70. A sidecut stream from the stripping section 26 is the butane product stream 17. A portion of the common bottoms stream 77 returns organic chloride compounds to the fractionation column 14 or to another lower pressure destination within the processing unit. The remainder of the common bottoms stream 77 may be returned to the divided wall column 70.

Figure 7:
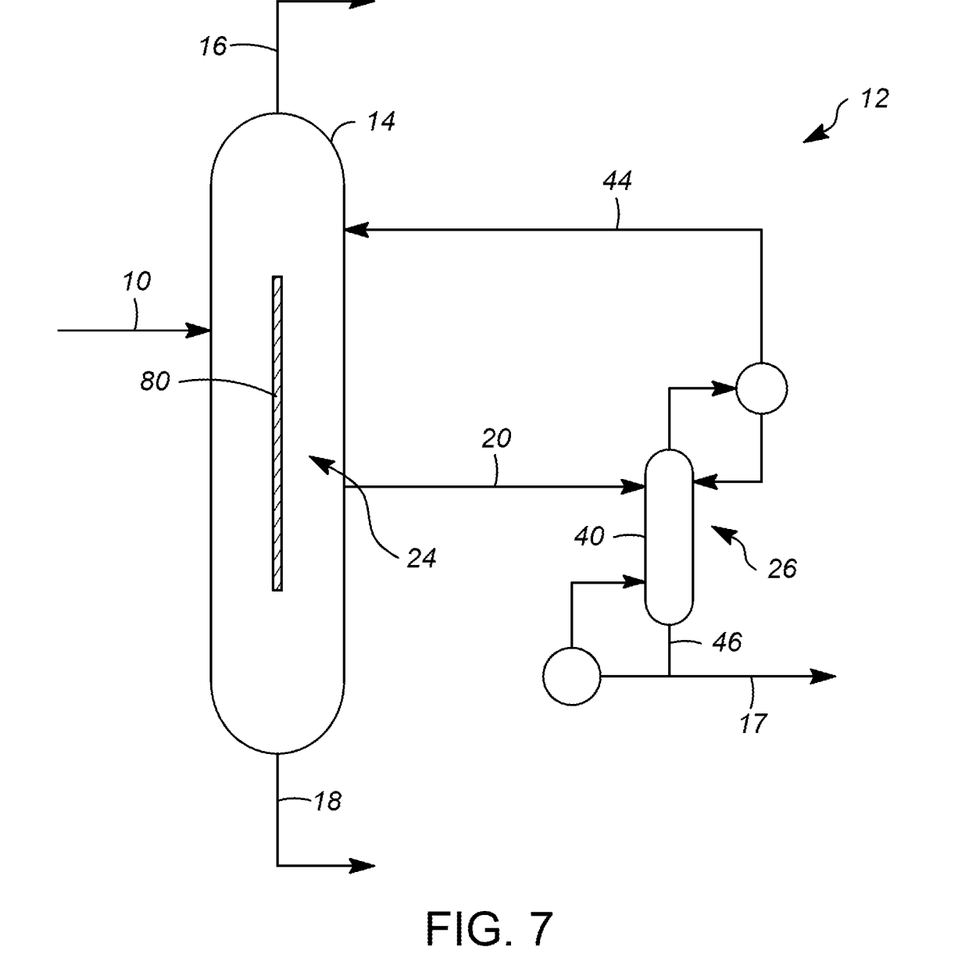
FIG. 7 is a further schematic process flow diagram according to one or more aspects of the present invention.
Figure 8:
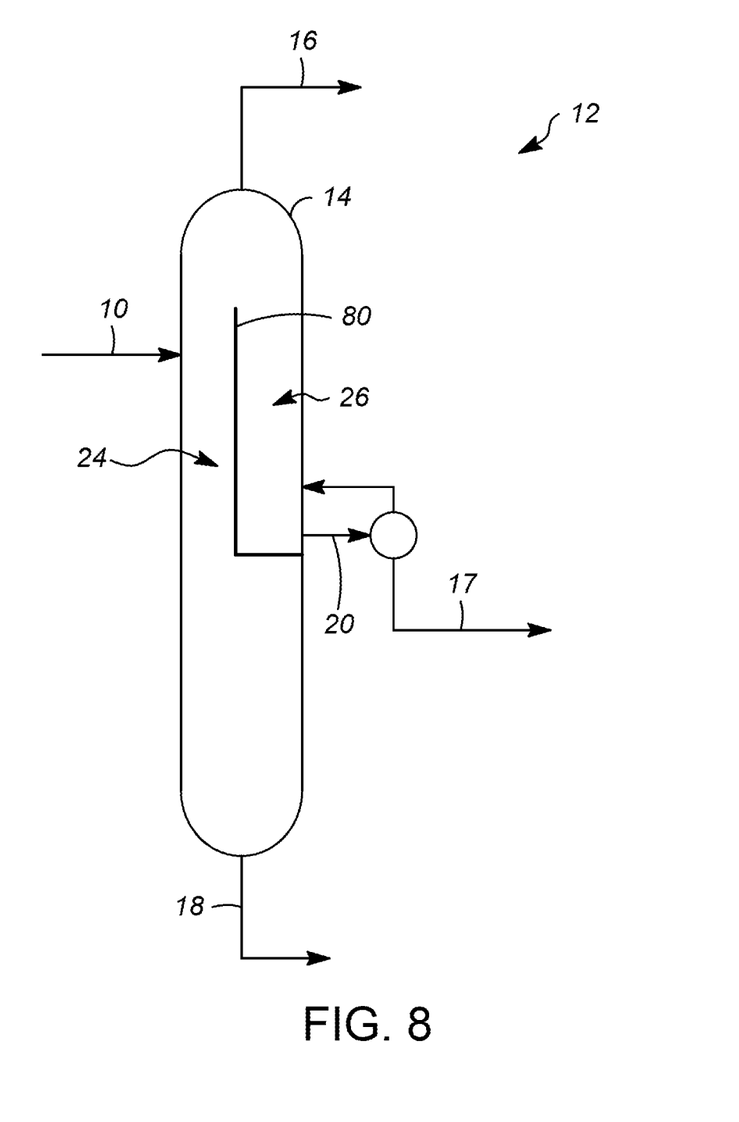
FIG. 8 is another schematic process flow diagram according to one or more aspects of the present invention; and, FIG. 9 is a schematic process flow diagram according to one or more aspects of the present invention.
Figure 9:
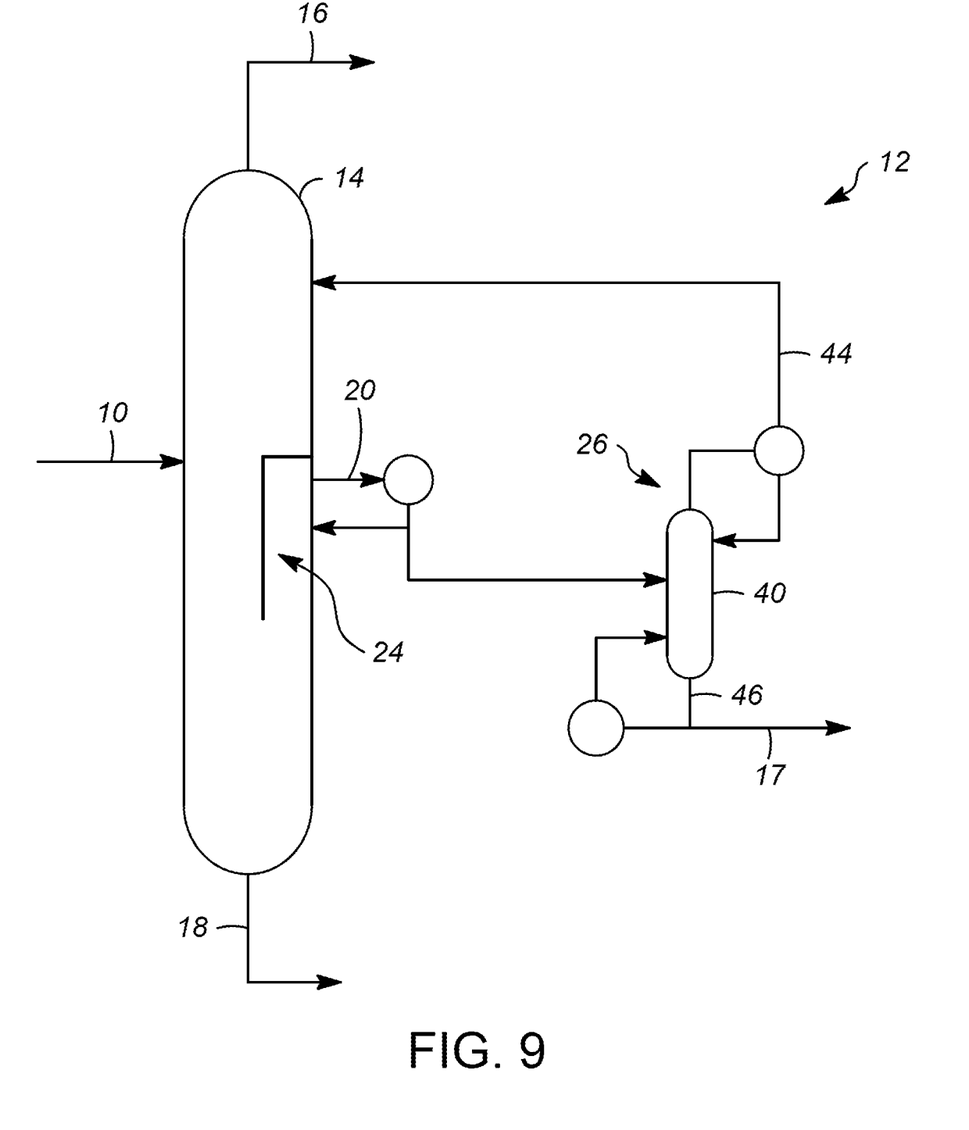

In FIGS. 7, 8, 9, the fractionation column 14 includes a wall 80 which provides at least the rectification section 24 in the fractionation column 14.

In FIG. 7, the separation zone 12 includes the stripper column 40 and a portion of the bottoms stream 46 from the stripper column is the butane product stream 17, while another portion is passed to a reboiler and then returned to the column 40. The overhead stream 44 from the stripper column 40 includes HCl, isobutane, and n-butane and is passed back to the fractionation column 14 or to another lower pressure destination within the processing unit. The n-butane flows downward in the rectification section 24 to remove organic chlorides to be removed in the bottoms stream 18 from the fractionation column 14.

In the embodiment of FIG. 8, the wall 80 in the fractionation column 14 provides both the rectification section 24 and the stripper section 26. The wall 80 extends above the injection point for the feed stream 10. The liquid side draw stream 20 is reboiled in a reboiler to provide stripping vapors to the fractionation column 14 and the liquid portion being the butane product stream 17.

In FIG. 9, the separation zone 12 again includes the stripper column 40 and a portion of the bottoms stream 46 from the stripper column 40 is the butane product stream 17. Again, a second portion of the bottoms stream 46 is passed to a reboiler before returning to the column 40. The liquid side draw stream 20 is cooled and passed to the stripper column 40. A portion may be refluxed back to the fractionation column 14. The overhead stream 44 from the stripper column 40, which includes HCl, is passed back to the fractionation column 14 or to another lower pressure destination within the processing unit.

In the various depicted aspects, both organic and inorganic chlorides are removed from a liquid portion of said feed stream in a rectification section of the separation zone. Additionally, stream 20 may either be a liquid draw stream which can be pumped or a vapor draw stream which may be vented to a lower pressure vessel or unit within the processing unit.

It should be appreciated and understood by those of ordinary skill in the art that various other components such as valves, pumps, filters, coolers, etc. were not shown in the drawings as it is believed that the specifics of same are well within the knowledge of those of ordinary skill in the art and a description of same is not necessary for practicing or understanding the embodiments of the present invention.

Any of the above lines, conduits, units, devices, vessels, surrounding environments, zones or similar may be equipped with one or more monitoring components including sensors, measurement devices, data capture devices or data transmission devices. Signals, process or status measurements, and data from monitoring components may be used to monitor conditions in, around, and on process equipment. Signals, measurements, and/or data generated or recorded by monitoring components may be collected, processed, and/or transmitted through one or more networks or connections that may be private or public, general or specific, direct or indirect, wired or wireless, encrypted or not encrypted, and/or combination(s) thereof; the specification is not intended to be limiting in this respect.

Signals, measurements, and/or data generated or recorded by monitoring components may be transmitted to one or more computing devices or systems. Computing devices or systems may include at least one processor and memory storing computer-readable instructions that, when executed by at least one processor, cause the one or more computing devices to perform a process that may include one or more steps. For example, the one or more computing devices may be configured to receive, from one or more monitoring component, data related to at least one piece of equipment associated with the process. The one or more computing devices or systems may be configured to analyze the data. Based on analyzing the data, the one or more computing devices or systems may be configured to determine one or more recommended adjustments to one or more parameters of one or more processes described herein. The one or more computing devices or systems may be configured to transmit encrypted or unencrypted data that includes the one or more recommended adjustments to the one or more parameters of the one or more processes described herein.

SPECIFIC EMBODIMENTS

While the following is described in conjunction with specific embodiments, it will be understood that this description is intended to illustrate and not limit the scope of the preceding description and the appended claims.

A first embodiment of the invention is a process for separating chlorides from a butane product stream, the process comprising separating, in a separation zone, a feed stream comprising light hydrocarbons, propane, isobutane, n-butane, chlorides, and C5+ hydrocarbons into a stream comprising light hydrocarbons, propane, isobutane, and n-butane and a liquid stream comprising an alkylate effluent with C5+ hydrocarbons; and, removing chlorides from a liquid or vapor portion of the feed stream in a rectification section of the separation zone, the rectification section providing a butane product stream. An embodiment of the invention is one, any or all of prior embodiments in this paragraph up through the first embodiment in this paragraph, wherein the separation zone comprises a fractionation column, and wherein the rectification section comprises a rectification column. An embodiment of the invention is one, any or all of prior embodiments in this paragraph up through the first embodiment in this paragraph, wherein a bottoms stream from the rectification column is passed back to the fractionation column. An embodiment of the invention is one, any or all of prior embodiments in this paragraph up through the first embodiment in this paragraph, wherein a side draw stream from the rectification column comprises the butane product stream. An embodiment of the invention is one, any or all of prior embodiments in this paragraph up through the first embodiment in this paragraph, wherein an overhead stream from the rectification column is condensed to provide the butane product stream. An embodiment of the invention is one, any or all of prior embodiments in this paragraph up through the first embodiment in this paragraph, wherein the separation zone comprises a fractionation column, and further comprises a stripping section. An embodiment of the invention is one, any or all of prior embodiments in this paragraph up through the first embodiment in this paragraph, wherein the stripping section and the rectification section are in the fractionation column. An embodiment of the invention is one, any or all of prior embodiments in this paragraph up through the first embodiment in this paragraph, wherein the separation zone comprises a second column and both the stripping section and the rectification section are in the second column. An embodiment of the invention is one, any or all of prior embodiments in this paragraph up through the first embodiment in this paragraph, wherein the separation zone further comprises a first column comprising the rectification section and a second column comprising the stripping section. An embodiment of the invention is one, any or all of prior embodiments in this paragraph up through the first embodiment in this paragraph, wherein a bottoms stream from the second column is passed to the first column. An embodiment of the invention is one, any or all of prior embodiments in this paragraph up through the first embodiment in this paragraph, wherein the first column and the second column produce a common overhead stream. An embodiment of the invention is one, any or all of prior embodiments in this paragraph up through the first embodiment in this paragraph, wherein the first column and the second column are disposed on top of each other. An embodiment of the invention is one, any or all of prior embodiments in this paragraph up through the first embodiment in this paragraph, wherein the separation zone comprises a second column and wherein the second column comprises the stripping section and the fractionation column comprises the rectification section.

A second embodiment of the invention is a process for separating chlorides from a butane product stream, the process comprising separating, in a separation zone comprising a deisobutanizer column, a feed stream comprising light hydrocarbons, propane, isobutane, n-butane, chlorides, and C5+ hydrocarbons into a stream comprising light hydrocarbons, propane, isobutane, and n-butane and a liquid stream comprising an alkylate effluent with C5+ hydrocarbons; and, passing a side draw stream from the deisobutanizer column to a rectification column, the side draw stream comprising liquid or vapor; passing a bottoms stream from the rectification column to the deisobutanizer column or another lower pressure vessel, the bottoms stream comprising organic chlorides; passing a vapor or liquid stream from the rectification column to the deisobutanizer column, the vapor or liquid stream comprising HCl, iso-butane, and n-butane; recovering a butane product stream from the deisobutanizer column; and, passing the butane product stream to an adsorbent zone having an adsorbent configured to remove chlorides and provide a chloride lean butane product stream. An embodiment of the invention is one, any or all of prior embodiments in this paragraph up through the second embodiment in this paragraph, wherein the butane product stream from the deisobutanizer column is a side draw stream. An embodiment of the invention is one, any or all of prior embodiments in this paragraph up through the second embodiment in this paragraph, further comprising cooling an overhead stream from the rectification column to provide the vapor or liquid stream and the butane product stream.

A third embodiment of the invention is a process for separating chlorides from an n-butane stream, the process comprising separating, in a separation zone comprising a separation column a feed stream comprising light hydrocarbons, propane, isobutane, n-butane, chlorides, and C5+ hydrocarbons into a stream comprising light hydrocarbons, propane, isobutane, and n-butane, and a liquid stream comprising an alkylate effluent with C5+ hydrocarbons; and, removing organic chlorides from the feed stream in a rectification section; and, removing HCl from the feed stream in a stripper section. An embodiment of the invention is one, any or all of prior embodiments in this paragraph up through the third embodiment in this paragraph, wherein the separation zone further comprises a first column comprising the rectification section and a second column comprising the stripping section. An embodiment of the invention is one, any or all of prior embodiments in this paragraph up through the third embodiment in this paragraph, wherein the rectification section is disposed within the separation column.

Without further elaboration, it is believed that using the preceding description that one skilled in the art can utilize the present invention to its fullest extent and easily ascertain the essential characteristics of this invention, without departing from the spirit and scope thereof, to make various changes and modifications of the invention and to adapt it to various usages and conditions. The preceding preferred specific embodiments are, therefore, to be construed as merely illustrative, and not limiting the remainder of the disclosure in any way whatsoever, and that it is intended to cover various modifications and equivalent arrangements included within the scope of the appended claims.

In the foregoing, all temperatures are set forth in degrees Celsius and, all parts and percentages are by weight, unless otherwise indicated.

While at least one exemplary embodiment has been presented in the foregoing detailed description of the invention, it should be appreciated that a vast number of variations exist. It should also be appreciated that the exemplary embodiment or exemplary embodiments are only examples, and are not intended to limit the scope, applicability, or configuration of the invention in any way. Rather, the foregoing detailed description will provide those skilled in the art with a convenient road map for implementing an exemplary embodiment of the invention, it being understood that various changes may be made in the function and arrangement of elements described in an exemplary embodiment without departing from the scope of the invention as set forth in the appended claims and their legal equivalents.

What is claimed is:

1. A process for separating chlorides from a butane product stream, the process comprising:
    separating, in a separation zone, a feed stream comprising light hydrocarbons, propane, isobutane, n-butane, chlorides, and C5+ hydrocarbons into a stream comprising light hydrocarbons, propane, isobutane, and n-butane and a liquid stream comprising an alkylate effluent with C5+ hydrocarbons; and,
    removing chlorides from a liquid or vapor portion of said feed stream in a rectification section of the separation zone, the rectification section providing a butane product stream.

2. The process of claim 1, wherein the separation zone comprises a fractionation column, and wherein the rectification section comprises a rectification column.

3. The process of claim 2, wherein a bottoms stream from the rectification column is passed back to the fractionation column.

4. The process of claim 3, wherein a side draw stream from the rectification column comprises the butane product stream.

5. The process of claim 3, wherein an overhead stream from the rectification column is condensed to provide the butane product stream.

6. The process of claim 1, wherein the separation zone comprises a fractionation column, and further comprises a stripping section.

7. The process of claim 6, wherein the stripping section and the rectification section are in the fractionation column.

8. The process of claim 6, wherein the separation zone comprises a second column and both the stripping section and the rectification section are in the second column.

9. The process of claim 6, wherein the separation zone further comprises a first column comprising the rectification section and a second column comprising the stripping section.

10. The process of claim 9, wherein a bottoms stream from the second column is passed to the first column.

11. The process of claim 9, wherein the first column and the second column produce a common overhead stream.

12. The process of claim 9, wherein the first column and the second column are disposed on top of each other.

13. The process of claim 6, wherein the separation zone comprises a second column and wherein the second column comprises the stripping section and the fractionation column comprises the rectification section.

14. A process for separating chlorides from a butane product stream, the process comprising:
    separating, in a separation zone comprising a deisobutanizer column, a feed stream comprising light hydrocarbons, propane, isobutane, n-butane, chlorides, and C5+ hydrocarbons into a stream comprising light hydrocarbons, propane, isobutane, and n-butane and a liquid stream comprising an alkylate effluent with C5+ hydrocarbons; and,
    passing a side draw stream from the deisobutanizer column to a rectification column, the side draw stream comprising liquid or vapor;
    passing a bottoms stream from the rectification column to the deisobutanizer column, the bottoms stream comprising organic chlorides;
    passing a vapor or liquid stream from the rectification column to the deisobutanizer column or another lower pressure vessel, the vapor or liquid stream comprising HCl, iso-butane, and n-butane;
    recovering a butane product stream from the deisobutanizer column; and,
    passing the butane product stream to an adsorbent zone having an adsorbent configured to remove chlorides and provide a chloride lean butane product stream.

15. The process of claim 14, wherein the butane product stream from the deisobutanizer column is a side draw stream.

16. The process of claim 14, further comprising:
    cooling an overhead stream from the rectification column to provide the vapor or liquid stream and the butane product stream.

17. A process for separating chlorides from an n-butane stream, the process comprising:
    separating, in a separation zone comprising a separation column a feed stream comprising light hydrocarbons, propane, isobutane, n-butane, chlorides, and C5+ hydrocarbons into a stream comprising light hydrocarbons, propane, isobutane, and n-butane, and a liquid stream comprising an alkylate effluent with C5+ hydrocarbons; and,
    removing organic chlorides from the feed stream in a rectification section; and, removing HCl from the feed stream in a stripper section.

18. The process of claim 17, wherein the separation zone comprises a first column comprising the rectification section and a second column comprising the stripper section.

19. The process of claim 17, wherein the rectification section is disposed within the separation column.

20. The process of claim 17, wherein the separation zone comprises a second column and both the stripper section and the rectification section are in the second column.

* * * * *